(12) United States Patent
Unger et al.

(10) Patent No.: US 10,086,218 B2
(45) Date of Patent: Oct. 2, 2018

(54) RESPIRATION SYSTEM

(71) Applicant: Dräger Safety AG & Co. KGaA, Lübeck (DE)

(72) Inventors: Jürgen Unger, Berlin (DE); David Cheesman, Bedlington (GB)

(73) Assignee: Dräger Safety AG & Co. KGaA, Lübeck (DE)

( * ) Notice: Subject to any disclaimer, the term of this patent is extended or adjusted under 35 U.S.C. 154(b) by 356 days.

(21) Appl. No.: 14/373,792

(22) PCT Filed: Feb. 5, 2013

(86) PCT No.: PCT/EP2013/052240
§ 371 (c)(1),
(2) Date: Jul. 22, 2014

(87) PCT Pub. No.: WO2013/117542
PCT Pub. Date: Aug. 15, 2013

(65) Prior Publication Data
US 2014/0345610 A1 Nov. 27, 2014

(30) Foreign Application Priority Data
Feb. 9, 2012 (DE) ........................ 10 2012 002 546

(51) Int. Cl.
*A62B 9/00* (2006.01)
*A61M 16/22* (2006.01)
(Continued)

(52) U.S. Cl.
CPC ............ *A62B 9/006* (2013.01); *A61M 16/22* (2013.01); *A62B 7/08* (2013.01); (Continued)

(58) Field of Classification Search
CPC .......... A62B 9/006; A62B 7/08; A62B 21/00; A62B 19/00; A61M 16/22;
(Continued)

(56) References Cited

U.S. PATENT DOCUMENTS 3,059,474 A * 10/1962 Keiler .................... G01K 1/143
116/207
3,911,413 A 10/1975 Wallace
(Continued)

FOREIGN PATENT DOCUMENTS

CN 85103668 A 11/1986
CN 1281738 A 1/2001
(Continued)

OTHER PUBLICATIONS

Chinese Office Action dated Nov. 8, 2015.

*Primary Examiner* — Gregory Anderson
*Assistant Examiner* — Margaret Luarca
(74) *Attorney, Agent, or Firm* — McGlew and Tuttle, P.C.

(57) ABSTRACT

A respiration system is provided with a container (1) in which, by an exothermic chemical reaction of a reaction material, $CO_2$ is removed from the respiration air or oxygen is generated, and with an indicator of the consumption of the reaction material. The consumption indicator has a predetermined amount (7) of material which can be melted by the reaction heat of the exothermic chemical reaction. The material is kept in thermal contact with the container interior in such a manner that a measurement of the total reaction heat, and thus the consumption of reactive material, can be read from the degree of melting of the meltable material.

18 Claims, 6 Drawing Sheets

(51) Int. Cl.
*A62B 7/08* (2006.01)
*A62B 19/00* (2006.01)
*A62B 21/00* (2006.01)

(52) U.S. Cl.
CPC .............. *A61M 2205/0227* (2013.01); *A61M 2205/0277* (2013.01); *A62B 19/00* (2013.01); *A62B 21/00* (2013.01)

(58) Field of Classification Search
CPC .... A61M 2205/0277; A61M 2205/022; A61M 2205/16; G01K 3/04; G01K 11/06; G01K 11/003; G01K 17/025; G01K 1/143; A61L 2/28
USPC ............ 128/202.26, 205.23, 202.22, 200.24, 128/205.12, 105.23, 205.27, 205.28; 374/160, 162, 45–50, 52–57, 100, 105, 374/161, 154, 195, 187; 116/207, 216
See application file for complete search history.

(56) References Cited

U.S. PATENT DOCUMENTS

| | | | | |
|---|---|---|---|---|
| 4,248,089 A | * | 2/1981 | Heinmets | G01K 11/06 374/162 |
| 4,762,423 A | * | 8/1988 | Basta | G01K 17/025 374/31 |
| 5,634,426 A | * | 6/1997 | Tomlinson | A62B 18/088 116/207 |
| 6,618,687 B2 | | 9/2003 | Warkander | |
| 2011/0017209 A1 | | 1/2011 | Monzyk | |
| 2013/0100983 A1 | * | 4/2013 | Meldrum | G01K 3/04 374/102 |

FOREIGN PATENT DOCUMENTS

| | | |
|---|---|---|
| CN | 101512318 A | 8/2009 |
| DE | 10 2005 015 275 B3 | 9/2006 |
| DE | 10 2005 026 838 B3 | 1/2007 |

* cited by examiner

RESPIRATION SYSTEM

CROSS REFERENCE TO RELATED APPLICATIONS

This application is a United States National Phase Application of International Application PCT/EP2013/052240 filed Feb. 5, 2013 and claims the benefit of priority under 35 U.S.C. § 119 of German Patent Application DE 10 2012 002 546.7 filed Feb. 9, 2012, the entire contents of which are incorporated herein by reference.

FIELD OF THE INVENTION

The present invention pertains to a respiration system with a container, in which $CO_2$ is removed from the breathing air or oxygen is generated by an exothermic chemical reaction of a reaction material, and with an indicator for the consumption of the reaction material.

BACKGROUND OF THE INVENTION

Respiration systems are, for example, closed-circuit respirators, which are defined as respirators independent from the ambient atmosphere, and in which respiration gas circulates. They are used where harmful effects due to toxic impurities contained in the breathing air or oxygen deficiency must be expected. The freely portable closed-circuit respirators supply the user of the device with respiration gas, which is carried along in the device, generated and purified. The maximum service life of the devices varies and depends on the quantity of respiration gas being carried along or generated in the device as well as the consumption of air by the user of the device. The oxygen reserve in the device is carried along in these devices either as pressurized oxygen or as chemical oxygen (e.g., potassium superoxide). The breathing air exhaled by the user of the device flows in closed-circuit devices into a regenerating cartridge, in which the carbon dioxide ($CO_2$) contained in the respiration gas is bound chemically. Among other things, water and a considerable quantity of reaction heat (approximately 113 kJ/mol) are generated in the process.

Exhaled $CO_2$ is bound by means of a chemical reaction in another application. If potassium superoxide is used as the reactant, this reacts with the moisture exhaled simultaneously with the $CO_2$ into oxygen, potassium hydroxide and potassium carbonate. Heat (169 kJ/mol) is likewise formed besides oxygen. Contrary to the regenerating cartridge, this process cannot be interrupted. Further hydroxides are also known, which may likewise be considered for use for binding $CO_2$ from the exhaled air. $H_2O$ and heat are likewise formed in these reactions.

Respirators that are used as anesthesia apparatuses in medical engineering use carbon dioxide absorbers to remove the carbon dioxide exhaled by the patient from the breathing gas. Various designs of such absorbers are available. Disposable absorbers are known, which are disposed of completely after use, and refillable devices are known. The absorbent (breathing lime) is filled as a bulk material into these; the absorbent is disposed of after use and is replaced with fresh breathing lime.

It is of great significance in all applications to provide an indicator for the consumption. The term "consumption" will be used hereinafter in a general sense and shall also cover variables derived therefrom, e.g., the residual capacity of the reacting material, i.e., the complement of the quantity of material consumed.

A color indicator, which signals the exhaustion of the breathing lime on the basis of the reaction moisture formed by a change in color, is added to the breathing lime in prior-art $CO_2$ absorbers used in medical engineering. The color change is read visually, but the limit of the color change often cannot be recognized unambiguously and the absorbers are therefore usually replaced at fixed intervals, regardless of whether or not their capacity has already been fully exhausted. An additional drawback of the color indicators is their reversibility, i.e., the color indicator returns to its original state after drying of the consumed breathing lime. It is therefore impossible to make a distinction between fresh and consumed (dried) breathing lime without a doubt. In addition, the odor and taste of the color indicator added are often felt to be at least unpleasant and a nuisance.

A respiration system of the type described in the introduction is known, for example, from DE 10 2005 015 275 A1, in which a method for determining the residual capacity of chemical canisters for use in oxygen-generating closed-circuit respirators is described. The number of breaths, the pressure level and the inhalation temperature are determined according to this patent, and the current breathing air consumption is determined from this and subtracted from the total capacity.

A respiration system, which recognizes the passage of the heat front generated during the $CO_2$ absorption via an array of temperature sensors and makes it possible to obtain information from this on the state of consumption of the breathing lime absorber, is described in U.S. Pat. No. 6,618,687.

A corresponding electronic system is needed in both systems, and a distinction between consumed and unconsumed material is not possible or is possible with a considerable effort only, for example, after an intermediate storage. In addition, cabled temperature sensors are led through housing walls in as gas-tight a manner as possible in order to guarantee the operation of the devices.

A memory chip, on which the current state of consumption is calculated from the operating data of the respiration system, stored and updated, is proposed in DE 10 2005 026 838 B3.

SUMMARY OF THE INVENTION

An object of the present invention is to design a respiration system with a consumption indicator, which indicates the state of consumption of carbon dioxide absorbers or of chemical cartridges generating oxygen, such that the degree of consumption of the reaction material is recognizable with certainty and that the consumption indication is irreversible and independent from the electric energy.

According to the invention, a respiration system is provided comprising a reaction material container comprising an inlet, an outlet and a container space receiving a reaction material in which $CO_2$ is removed from breathing gas or oxygen is generated by an exothermic chemical reaction of a reaction material as the breathing gas passes through the container space from the inlet to the outlet. The respiration system further comprises a consumption indicator indicating a consumption of the reaction material. The consumption indicator comprises an indicator material container and indicator material within the indicator material container. The indicator material is meltable by the reaction heat of the exothermic chemical reaction. The indicator material container is in thermal contact with the reaction material container. The consumption indicator provides an indication of a total reaction heat and a consumption of reaction material based on a degree of melting of the indicator material.

According to the present invention, the consumption indicator has a preset quantity of material, which is meltable by the reaction heat of the exothermic chemical reaction and is kept thermally in contact with the container interior, e.g., by being in contact with the wall of the container. The visible degree of melting of the preset quantity of meltable material is an indicator of the integrated reaction heat, which has altogether acted on the meltable material, and thus it provides an indication of the consumption of reactive material.

In an advantageous embodiment, the consumption indicator comprises the reaction material container as a tube, one end of which adjoins the reaction material container. A bar of the meltable material is kept in thermal contact with the outer wall of the reaction material container.

A spring, which acts on the bar of meltable material in order to press same with one end against the container, is provided in the tube in an advantageous embodiment.

The outer wall of the tube is at least partially transparent in an advantageous embodiment, so that the remaining (unmelted) length of the bar of meltable material is visible.

The solid, but meltable material has a melting point, which is selected to be such that the meltable material melts at the temperatures generated by the exothermic chemical reaction. The meltable material is kept thermally in contact with the container, in which the chemical reaction for absorbing $CO_2$ or for generating oxygen takes place. The meltable material is increasingly melted during the continuous chemical reaction, so that the quantity of melted material or the rest of the yet unmelted material is an indicator of the integrated reaction heat and hence an indicator of the degree of consumption of the reaction material. The quantity of meltable material may be selected, for example, such that the heat generated as a whole in case of complete consumption of the reaction material is so large that the meltable material is melted completely. If the meltable material is melted completely, this is therefore an indication that the reaction material has reacted completely and the residual capacity is therefore zero. The relative percentage of yet unmelted meltable material therefore provides information on the degree of consumption of the reaction material and is at the same time irreversible.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
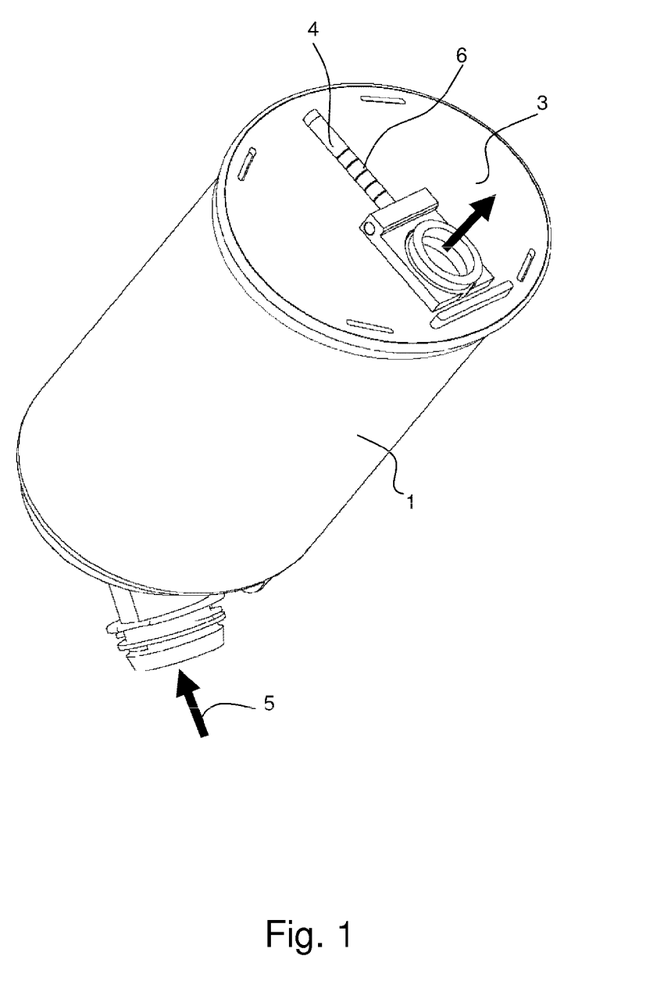
FIG. 1 is a perspective view of a container containing reaction material, through which container breathing gas flows.
Figure 2:
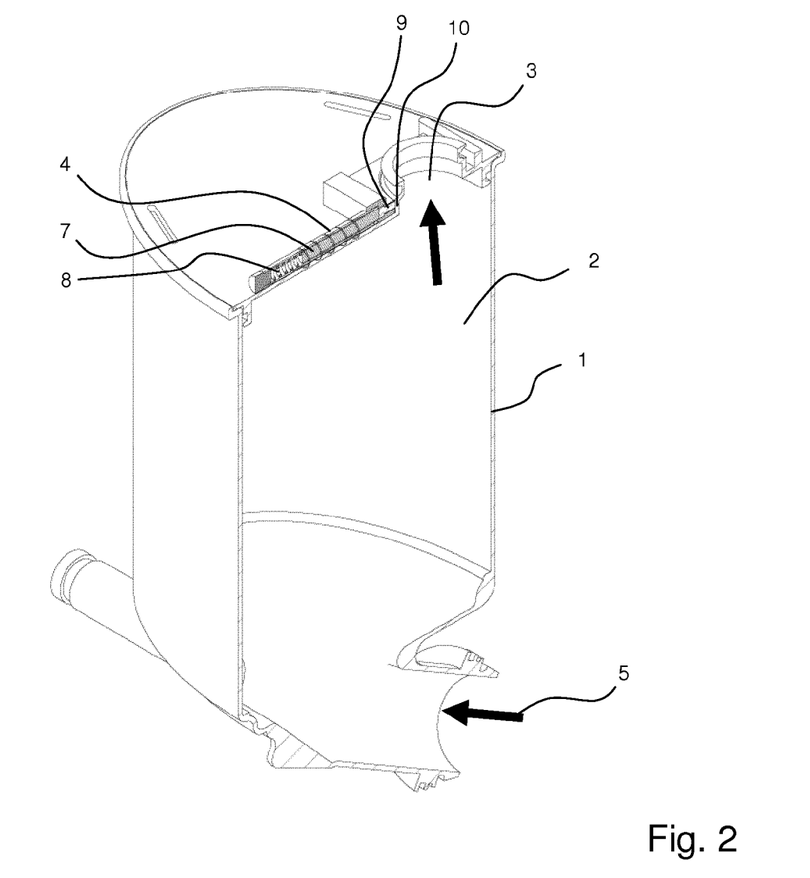
FIG. 2 is a sectional view of the container from FIG. 1.
Figure 3:
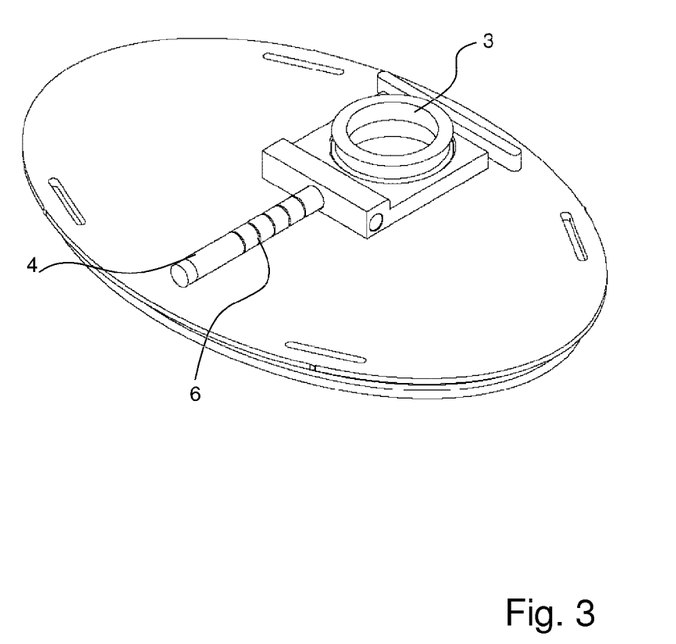
FIG. 3 is an enlarged view of the cover of the container.

Referring to the drawings in particular, FIGS. 1 and 2 show a container 1, through which breathing gas flows, the breathing gas entering at the inlet 5 and leaving the container at the outlet 3. Reaction material 2, in this case breathing lime for binding $CO_2$, is contained in the container 1. A tube 4 made of a transparent material with poor heat conduction, e.g., a plastic tube, is arranged on the container 1 at the outlet 3. A rod 7 or a bar 7 of meltable material, for example, stearin, which melts at about 50° C., is present in the tube 4. The meltable material is kept with one end, which is located at the open end of the tube, in thermal contact with the container interior, in this case in contact with the wall at the outlet 3 for the breathing gas. The end of the rod 7 that has thermal contact with the reaction material may be in contact, e.g., with a probe tip 9 consisting of a material having very good heat conductivity, which is in contact with the housing wall 10. As an alternative, the probe tip may also have an elongated design and reach the reaction material in the container interior with one end.

Figure 5:
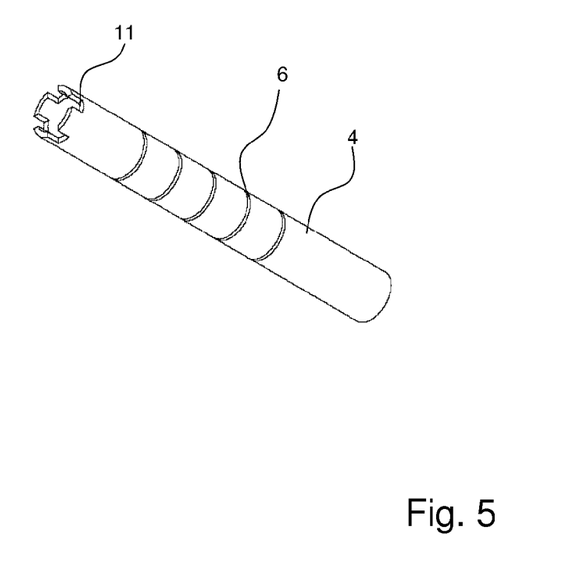
FIG. 5 is a perspective view of a tube for a respiration system with consumption indicator.

As is shown in FIG. 5, the tube 4 is provided with one or more perforations 11 at its end that is in thermal contact with the container interior. The perforations 11 make it possible for the melted material to flow off from the tube 4.

Figure 4:
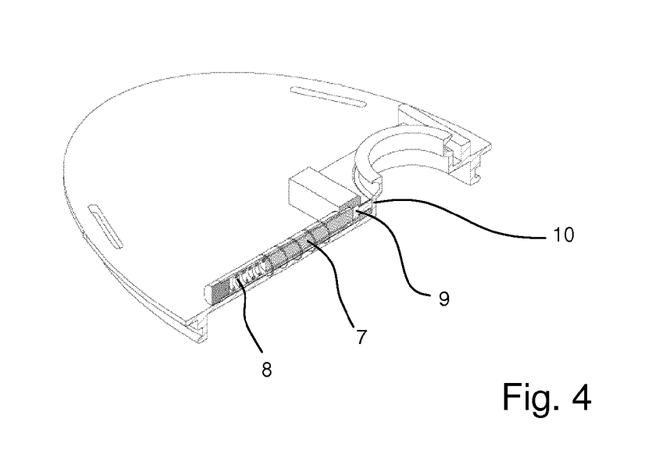
FIG. 4 is a sectional view of the cover from FIG. 3.

As is shown in FIGS. 2 and 4, a compression spring 8, which presses the rod 7 consisting of meltable material against the container wall 10 with one end, is arranged in the tube 4, so that the rod is pressed by the spring 8 in the direction of the end of the rod with thermal contact as the melting of the rod advances. The length of the rod 7 of unmelted material decreases in this manner continually as the chemical reaction progresses in the container. Marks 6, with which the remaining length of the rod 7 of meltable material can be read, may be provided on the tube 4.

It is also possible to provide sensors, with which the change in length or the remaining length of the rod 7 of meltable material can be detected. This change in length can then be analyzed and displayed.

Figure 6:
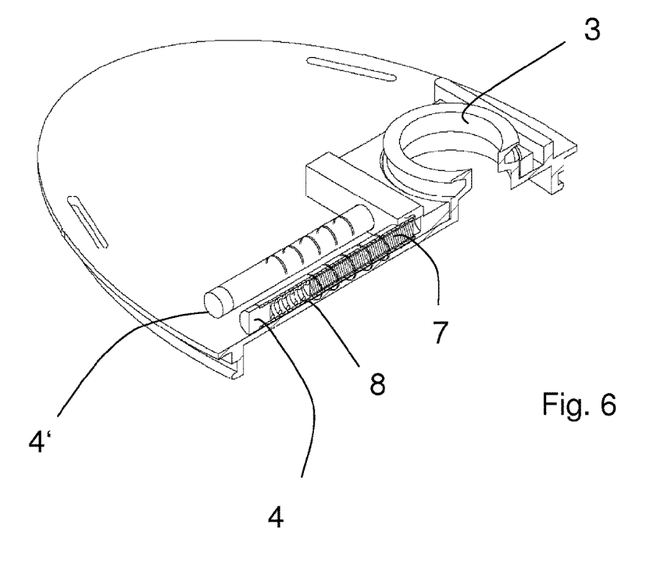
FIG. 6 is an enlarged view of the cover of an alternative embodiment of the container.

If the containers with consumption indicator are used or stored at temperatures that come close to the melting point of the meltable material, provisions may be made for having ready an additional quantity of the same meltable material, which is not, however, in thermal contact with the container interior and the reaction material. A second tube 4' is provided next to the tube 4 in FIG. 6, and the end facing the outlet 3 is thermally insulated against the container material, e.g., by a heat insulator. The percentage of melting that is not based on the reaction heat of the reaction material can be determined by such a redundant "consumption indicator" by comparing the meltable materials with and without thermal contact with the container. Furthermore, it can thus be determined at the same time whether and how long, e.g., a maximum allowable storage temperature was exceeded.

While specific embodiments of the invention have been shown and described in detail to illustrate the application of the principles of the invention, it will be understood that the invention may be embodied otherwise without departing from such principles.

The invention claimed is:

1. A respiration system comprising:
   a container, in which $CO_2$ is removed from the breathing air or oxygen is generated by an exothermic chemical reaction of a reaction material; and
   a consumption indicator for the consumption of the reaction material, wherein the consumption indicator has a preset quantity of indicator material, which is meltable by the reaction heat of the exothermic chemical reaction and which is kept in thermal contact with the container interior, and the consumption indicator is configured such that the visible degree of melting of the preset quantity of meltable material is an indicator of the integrated reaction heat of the exothermic chemical reaction of the reaction material, which has altogether acted on the meltable material based on the thermal contact, and provides a visible indication of the consumption of reactive material, so that an indication of the total reaction heat and hence of the consumption of reactive material can be read from the visible degree of melting of the meltable material, wherein the consumption indicator further comprises an indicator material advancement means for advancing unmelted indicator material towards a region of the thermal contact between the consumption indicator and the container interior.

2. A respiration system in accordance with claim 1, wherein the consumption indicator has a tube, one end of which is in contact with the container for the reaction material and in which a bar of the meltable indicator material is kept in thermal contact with a wall of the container.

3. A respiration system in accordance with claim 2, wherein the indicator material advancement means comprises a spring, which acts on the bar of meltable material in order to press the bar of meltable material with one end against the container, and the spring is provided in the tube.

4. A respiration system in accordance with claim 2, wherein an outer wall of the tube is at least partly transparent.

5. A respiration system in accordance with claim 4, wherein marks are provided as a length gradation along the tube on the transparent parts of the outer wall of the tube.

6. A respiration system in accordance with claim 1, further comprising another indicator comprising a tube and a second preset quantity of material meltable by the reaction heat of the exothermic chemical reaction, which is not in thermal contact with the container interior.

7. A respiration system in accordance with claim 1, wherein consumption indicator further comprises a probe tip and the meltable material is in thermal contact with the container interior via the probe tip comprised of a material with good heat conductivity.

8. A respiration system in accordance with claim 7, wherein the probe tip has an extent that reaches into the reactive material present in the container interior.

9. A respiration system comprising:
a reaction material container comprising an inlet, an outlet and a container space receiving a reaction material in which $CO_2$ is removed from breathing gas or oxygen is generated by an exothermic chemical reaction of a reaction material as the breathing gas passes through the container space from the inlet to the outlet; and
a consumption indicator indicating a consumption of the reaction material, the consumption indicator comprising an indicator material container and a preset quantity of indicator material within the indicator material container, the indicator material being meltable by the reaction heat of the exothermic chemical reaction, the indicator material container being in thermal contact with the reaction material container to increasingly melt during the exothermic chemical reaction of the reaction material and the indicator material container and the preset quantity of indicator material within the indicator material container being configured to visibly show a total quantity of melted indicator material, indicating an integrated reaction heat of the exothermic chemical reaction of the reaction material, which has altogether acted on the indicator material based on the thermal contact, whereby melting of the indicator provides an indication of a total reaction heat and a consumption of reaction material based on a visible degree of melting of the indicator material, wherein the consumption indicator further comprises a probe tip comprising a thermally conductive material providing thermal contact between the meltable indicator material and the container interior.

10. A respiration system in accordance with claim 1, wherein:
the indicator material container comprises a tube with one tube end in contact with the reaction material container;
the indicator material is in the form of a bar, in an un-melted state;
the bar of the indicator material is kept in thermal contact with a wall of the reaction material container.

11. A respiration system in accordance with claim 10, further comprising a spring acting on the bar of indicator material to press the bar of indicator material against the reaction material container.

12. A respiration system in accordance with claim 10, wherein an outer wall of the tube is at least partly transparent.

13. A respiration system in accordance with claim 12, wherein marks are provided as a length gradation along the tube on transparent parts of the outer wall of the tube.

14. A respiration system in accordance with claim 10, wherein the consumption indicator further comprises another indicator material container and a second preset quantity of meltable indicator material, the second preset quantity of indicator material being meltable by the reaction heat of the exothermic chemical reaction, the another indicator material container not being in thermal contact with the reaction material container interior.

15. A respiration system in accordance with claim 9, wherein the probe tip reaches into the reactive material present in the container interior.

16. A respiration system comprising:
a reaction material container comprising an inlet, an outlet and a container space with a reaction material in which $CO_2$ is removed from breathing gas or oxygen is generated by an exothermic chemical reaction of a reaction material as the breathing gas passes through the container space from the inlet to the outlet; and
a consumption indicator comprising:
an indicator material container;
a quantity of indicator material within the indicator material container, the indicator material container being disposed in thermal contact with the reaction material container to increasingly melt the indicator material during the exothermic chemical reaction of the reaction material with the indicator material melting continually as the chemical reaction progresses in the container, the consumption indicator being configured such that the visible degree of melting of the preset quantity of meltable material is an indicator of the integrated reaction heat, which has altogether acted on the meltable material, and provides a visible indication of the consumption of reactive material, whereby a quantity of the indicator material that has melted indicates an integrated reaction heat of the exothermic chemical reaction of a reaction material and a consumption of reaction material, wherein the consumption indicator further comprises an indicator material advancement means for advancing unmelted indicator material towards a region of thermal contact between the indicator material container and the reaction material.

17. A respiration system in accordance with claim 16, wherein:
- the indicator material container comprises a tube with one tube end in contact with the reaction material container;
- the indicator material is in the form of a bar, in an un-melted state;
- the consumption indicator further comprises a spring acting on the bar of indicator material to press the bar of indicator material toward the reaction material container to maintain the indicator material in thermal contact with the reaction material container.

18. A respiration system in accordance with claim 16, wherein the consumption indicator further comprises a probe tip comprising a thermally conductive material providing thermal contact between the meltable indicator material and the container interior.

* * * * *